(12) United States Patent
Muraoka et al.

(10) Patent No.: US 10,281,420 B2
(45) Date of Patent: May 7, 2019

(54) GAS-DETECTING APPARATUS INCLUDING GAS SENSOR AND METHOD OF DETECTING HYDROGEN USING GAS SENSOR

(71) Applicant: Panasonic Intellectual Property Management Co., Ltd., Osaka (JP)

(72) Inventors: Shunsaku Muraoka, Osaka (JP); Kazunari Homma, Kyoto (JP); Zhiqiang Wei, Osaka (JP); Koji Katayama, Nara (JP)

(73) Assignee: Panasonic Intellectual Property Management Co., Ltd., Osaka (JP)

( * ) Notice: Subject to any disclaimer, the term of this patent is extended or adjusted under 35 U.S.C. 154(b) by 0 days.

(21) Appl. No.: 15/472,979

(22) Filed: Mar. 29, 2017

(65) Prior Publication Data

US 2017/0307557 A1 Oct. 26, 2017

(30) Foreign Application Priority Data

Apr. 26, 2016 (JP) .................................. 2016-088143

(51) Int. Cl.
*G01N 27/12* (2006.01)
*G01N 33/00* (2006.01)

(52) U.S. Cl.
CPC ......... *G01N 27/125* (2013.01); *G01N 33/005* (2013.01)

(58) Field of Classification Search
CPC ........................... G01N 27/125; G01N 33/005
See application file for complete search history.

(56) References Cited

U.S. PATENT DOCUMENTS 8,188,833 B2 * 5/2012 Tsuji .................. H01L 45/1246
257/246
2002/0187075 A1 12/2002 Nadanami et al.
(Continued)

FOREIGN PATENT DOCUMENTS

EP 266840 5/1988
JP 59-058348 4/1984
(Continued)

OTHER PUBLICATIONS

Song, Junghui, et al. "AlGaN/GaN Schottky diode hydrogen sensor performance at high temperatures with different catalytic metals." Solid-state electronics 49.8 (2005): 1330-1334.*
(Continued)

*Primary Examiner* — Robert J Eom
(74) *Attorney, Agent, or Firm* — McDermott Will & Emery LLP

(57) ABSTRACT

A gas-detecting apparatus includes a gas sensor and a power supply circuit. The gas sensor includes: a first electrode; a second electrode; a metal oxide layer disposed between the first electrode and the second electrode; and an insulation film covering the first electrode, the second electrode, and the metal oxide layer. The insulation file having an opening from which a surface of the second electrode is exposed. The resistance value of the metal oxide layer decreases when gas containing hydrogen atoms comes into contact with the second electrode. The power supply circuit applies a predetermined voltage between the first electrode and the second electrode to increase the resistance value of the metal oxide layer before and/or after the decrease in the resistance value of the metal oxide layer.

19 Claims, 9 Drawing Sheets

(56) References Cited

U.S. PATENT DOCUMENTS

2010/0025241 A1  2/2010  Hane et al.
2013/0000280 A1  1/2013  Korenev
2013/0071986 A1  3/2013  Deweerd et al.

FOREIGN PATENT DOCUMENTS

JP   61-191954   8/1986
JP   63-126857   5/1988
JP   11-160267   6/1999

OTHER PUBLICATIONS

Fog, Agner, and Richard P. Buck. "Electronic semiconducting oxides as pH sensors." Sensors and Actuators 5.2 (1984): 137-146.*
J. Yu et al., "Hydrogen gas sensing properties of Pt/Ta2O5 Schottky diodes based on Si and SiC substrates", Sensors and Actuators A 172, pp. 9-14, Available online Feb. 25, 2011.

* cited by examiner

100

GAS-DETECTING APPARATUS INCLUDING GAS SENSOR AND METHOD OF DETECTING HYDROGEN USING GAS SENSOR

BACKGROUND

1. Technical Field

The present disclosure relates to a gas-detecting apparatus including a gas sensor.

2. Description of the Related Art

Japanese Unexamined Patent Application Publication No. 59-58348 discloses a gas sensor detecting the presence of hydrogen gas as a change in resistance value. This gas sensor includes a tantalum pentoxide ($Ta_2O_5$) material containing palladium (Pd) and glass and includes platinum (Pt) electrodes having the material therebetween.

Sensors and Actuators A, 172 (2011), 9-14 discloses a Pt/$Ta_2O_5$ shot key diode for hydrogen sensing. In the shot key diode, hydrogen molecules are dissociated into hydrogen atoms on the surface of catalytic Pt.

SUMMARY

In one general aspect, the techniques disclosed here feature a gas-detecting apparatus including a gas sensor and a power supply circuit. The gas sensor includes: a first electrode; a second electrode; a metal oxide layer disposed between the first electrode and the second electrode, the metal oxide layer including a bulk area and a local area surrounded by the bulk area, a degree of oxygen deficiency of the local area being higher than that of the bulk area; and an insulation film covering the first electrode, the second electrode, and the metal oxide layer, the insulation film having an opening from which a surface of the second electrode is exposed. The resistance value of the metal oxide layer is decreased when gas containing hydrogen atoms comes into contact with the second electrode. The power supply circuit applies a predetermined voltage between the first electrode and the second electrode to increase the resistance value of the metal oxide layer before and/or after the resistance value is decreased by the contact of the gas.

It should be noted that general or specific embodiments may be implemented as a system, a method, an integrated circuit, a computer program, a storage medium, or any selective combination thereof.

Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

DETAILED DESCRIPTION

Figure 1A:
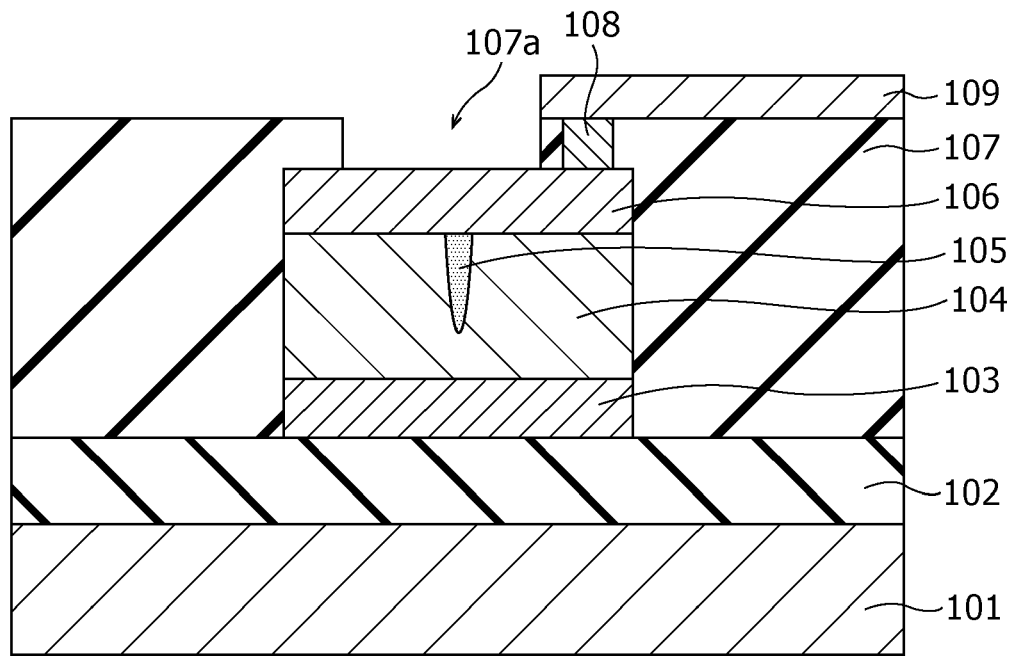
FIG. 1A is a cross-sectional view illustrating an example of a gas sensor according to an embodiment.

Underlying Knowledge Forming Basis of the Present Disclosure

The present inventors have diligently studied and, as a result, have found that known gas sensors have the following disadvantages.

In known gas sensors, elements detecting gas are heated to 100° C. or more for improving the sensitivity in detection of hydrogen-containing gas. Consequently, the power consumption in known gas sensors is about 100 mW at the lowest. Accordingly, if such a gas sensor is used in the ON-state at all times, a problem of increasing the power consumption is caused.

A gas-detecting apparatus according to an aspect of the present disclosure can detect hydrogen-containing gas with high sensitivity and has excellent power-saving properties.

Embodiments of the present disclosure will now be described with reference to the drawings.

In the drawings, elements having substantially the same structures, behaviors, and effects are denoted by the same reference symbols, and duplicate explanations are omitted. The numerical values, materials, compositions, shapes, methods of forming films, connection relationships between components, and other factors described below are all mere examples for specifically describing embodiments of the present disclosure, and the present disclosure is not limited to these examples. Among the components in the following embodiments, the components not described in independent claims showing the highest-order concept will be described as arbitrary components.

First Embodiment

[Structure of Gas Sensor]

A gas sensor according to First Embodiment has a metal-insulator-metal (MIM) lamination structure composed of a resistive film (metal oxide layer) and metal films. The gas sensor can detect hydrogen-containing gas by utilizing self-heating and gas sensitivity of a local area formed in the resistive film without heating with a heater. Herein, the hydrogen-containing gas is a collective term of gases composed of molecules containing hydrogen atoms and can include, for example, hydrogen, methane, and alcohol.

FIG. 1A is a cross-sectional view illustrating an example of the structure of a gas sensor 100 according to First Embodiment.

Figure 1B:
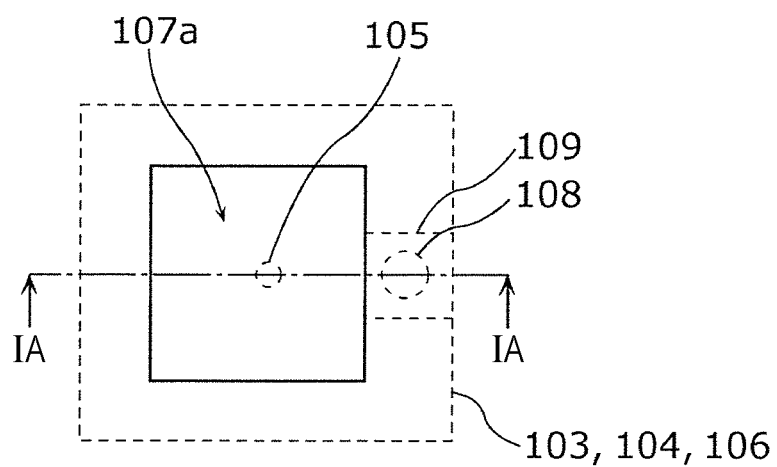
FIG. 1B is a top view illustrating the example of the gas sensor according to the embodiment.

FIG. 1B is a top view illustrating the example of the structure of the gas sensor 100 according to First Embodiment. The cross-section shown in FIG. 1A corresponds to the cross-section viewed along the cutting line IA-IA of FIG. 1B in the arrow direction.

The gas sensor 100 includes a substrate 101, an insulation film 102 formed on the substrate 101, a first electrode 103 and a second electrode 106 formed above the insulation film 102, a resistive film 104 disposed between the first electrode 103 and the second electrode 106, an insulation film 107, a via 108, and a wiring 109. A main surface of the first electrode 103 and a main surface of the second electrode 106 face each other. The resistive film 104 is disposed so as to be in contact with the main surface of the first electrode 103 and the main surface of the second electrode 106.

The insulation film 107 is provided with an opening 107a for bringing the gas as an object to be detected into contact with the second electrode 106. In other words, the insulation film 107 covers the first electrode 103, the second electrode 106, and the resistive film 104 in such a manner that at least a part of the upper surface (the other surface opposite to the main surface) of the second electrode 106 is exposed without being covered with the insulation film 107.

The resistive film 104 lies between the first electrode 103 and the second electrode 106 and reversibly changes the resistance value based on the electrical signal applied between the first electrode 103 and the second electrode 106. For example, the resistive state of the resistive film 104 reversibly transitions between a high resistive state and a low resistive state depending on the voltage (potential difference) applied between the first electrode 103 and the second electrode 106. The resistive state of the resistive film 104 transitions, for example, from the high resistive state to the low resistive state depending on the hydrogen-containing gas brought into contact with the second electrode 106.

Herein, the inside of the resistive film 104 includes a local area 105 being in contact with the second electrode 106 and not being in contact with the first electrode 103. The local area 105 has a degree of oxygen deficiency higher than that of its circumference (i.e., the bulk area of the resistive film 104). The degree of oxygen deficiency of the local area 105 reversibly changes depending on application of an electrical signal between the first electrode 103 and the second electrode 106 and the presence or absence of hydrogen-containing gas in the gas being in contact with the second electrode 106. The local area 105 is a minute region containing a filament (conductive path) consisting of an oxygen defect site.

In the portion of the insulation film 107 covering the upper surface of the second electrode 106, the via 108 passes through the insulation film 107 and is connected to the second electrode 106. The wiring 109 is disposed on the via 108.

In the present disclosure, the "degree of oxygen deficiency" of a metal oxide is a ratio of the amount of the oxygen deficit in the metal oxide to the amount of oxygen in the oxide having a stoichiometric composition consisting of the same elements as those of the metal oxide (herein, the amount of the oxygen deficit is the value obtained by subtracting the amount of oxygen in the metal oxide from the amount of oxygen in the metal oxide having a stoichiometric composition). If the same elements as those of the metal oxide can form a plurality of metal oxides having stoichiometric compositions, the degree of oxygen deficiency of the metal oxide is defined based on one having the highest resistance value among the metal oxides having the stoichiometric compositions. The metal oxide having the stoichiometric composition is more stable and has a higher resistance value compared to metal oxides having other compositions.

For example, if the metal is tantalum (Ta), the oxide having the stoichiometric composition according to the above-described definition is $Ta_2O_5$ and can be expressed as $TaO_{2.5}$. The degree of oxygen deficiency of $TaO_{2.5}$ is 0%, and the degree of oxygen deficiency of $TaO_{1.5}$ is (2.5−1.5)/2.5, i.e., 40%. In an oxygen-excess metal oxide, the degree of oxygen deficiency is a negative value. In the present disclosure, the degree of oxygen deficiency can be a positive value, zero, or a negative value, unless otherwise specified.

An oxide having a low degree of oxygen deficiency is more similar to the oxide having the stoichiometric composition and therefore has a high resistance value, while an oxide having a high degree of oxygen deficiency is more similar to the metal constituting the oxide and therefore has a low resistance value.

The term "oxygen content" is the rate of the number of oxygen atoms based on the total number of all atoms. For example, the oxygen content of $Ta_2O_5$ is the rate ($O/(Ta+O)$) of the number of oxygen atoms based on the total number of all atoms, i.e., 71.4 atm %. Accordingly, an oxygen-deficient tantalum oxide has an oxygen content higher than 0 atm % and less than 71.4 atm %.

The local area 105 is formed in the resistive film 104 by applying an initial break voltage between the first electrode 103 and the second electrode 106. In other words, the initial break voltage is a voltage applied between the first electrode 103 and the second electrode 106 for forming the local area 105. The absolute value of the initial break voltage may be higher than that of the write-in voltage. The write-in voltage is a voltage applied between the first electrode 103 and the second electrode 106 for causing reversible transition between the high resistive state and the low resistive state of the resistive film 104. Alternatively, the absolute value of the initial break voltage may be less than that of the write-in voltage. In such a case, the initial break voltage may be repeatedly applied or may be continuously applied for a predetermined period of time. As shown in FIG. 1A, the application of the initial break voltage forms a local area 105 being in contact with the second electrode 106 and not being in contact with the first electrode 103.

The local area 105 is conceived to contain a filament (conductive path) consisting of an oxygen defect site. The local area 105 has a minute size matching with the filament necessary for current to flow. The formation of the filament in the local area 105 will be described using a percolation model.

The percolation model is based on a theory that a density of oxygen defect sites exceeding a threshold increases the probability of forming a connection of oxygen defect sites in an assumed random distribution of the oxygen defect sites in the local area 105.

In the percolation model, a filament is formed by connection of a plurality of oxygen defect sites in the local area 105. The change in resistance of the resistive film 104 is caused through generation and disappearance of oxygen defect sites in the local area 105.

Herein, the term "oxygen defect" refers to that oxygen in a metal oxide is deficient compared to that of the stoichiometric composition. The term "density of oxygen defect sites" corresponds to the degree of oxygen deficiency. That is, the density of oxygen defect sites increases with the degree of oxygen deficiency.

The local area 105 may be formed at only one region of the resistive film 104 of the gas sensor 100. The number of local areas 105 formed in the resistive film 104 can be determined by, for example, electron beam absorbed current (EBAC) analysis.

If the local area 105 is present in the resistive film 104, the current flowing in the resistive film 104 by application of a voltage between the first electrode 103 and the second electrode 106 is concentrated in the local area 105.

The local area 105 has a small size and therefore generates heat by, for example, a current of about several tens of microamperes flowing at the time of reading out the resistance value. This heat generation causes a considerable increase in the temperature. The power consumption when a current of about several tens of microamperes flows is less than 0.1 mW.

The second electrode 106 is made of a metal (e.g., Pt) having a catalytic action, and the local area 105 is in contact with the second electrode 106. In this structure, the second electrode 106 is heated by the heat generated in the local area 105 to efficiently release hydrogen atoms from hydrogen-containing gas.

If the gas as an object to be tested contains hydrogen-containing gas, hydrogen atoms are released from the hydrogen-containing gas at the second electrode 106, and the released hydrogen atoms bind to oxygen atoms in the local area 105 to reduce the resistance value of the local area 105.

The gas sensor 100 thus has characteristics of decreasing the resistance value between the first electrode 103 and the second electrode 106 by the contact of the second electrode 106 with hydrogen-containing gas. Such characteristics allow the detection of hydrogen-containing gas contained in the gas as an object to be tested by detecting a reduction in the resistance value between the first electrode 103 and the second electrode 106 caused by the contact of the gas with the second electrode 106.

Furthermore, even if the local area 105 is in any of the high resistive state and the low resistive state, the resistance value is decreased by the contact of hydrogen-containing gas with the second electrode 106. Accordingly, the gas sensor 100 can detect hydrogen-containing gas, even if the local area 105 is in any of the high resistive state and the low resistive state. However, in order to more clearly detect a reduction in the resistance value, the local area 105 may be electrically set to a high resistive state, previous to the use of the gas sensor 100.

The details of the gas sensor 100 for obtaining stable resistance change characteristics will now be described.

The resistive film 104 is made of an oxygen-deficient metal oxide. The mother metal of the metal oxide may be at least one selected from transition metals, such as tantalum (Ta), hafnium (Hf), titanium (Ti), zirconium (Zr), niobium (Nb), tungsten (W), nickel (Ni), and iron (Fe); and aluminum (Al). Since transition metals have multiple oxidation states, different resistive states can be achieved by a redox reaction.

Herein, an oxygen-deficient metal oxide is a metal oxide having a higher degree of oxygen deficiency compared to a metal oxide having the stoichiometric composition consisting of the same metal elements. The oxygen-deficient metal oxide typically has semiconductor characteristics, while the metal oxide having the stoichiometric composition is typically an insulator. The gas sensor 100 can achieve high reproducibility and stable resistance change behavior by using an oxygen-deficient metal oxide for the resistive film 104.

For example, if the metal oxide constituting the resistive film 104 is hafnium oxide represented by $HfO_x$ in which the value x is 1.6 or more, the resistive film 104 can stably change the resistance value. In such a case, the hafnium oxide film may have a thickness of 3 to 4 nm.

If the metal oxide constituting the resistive film 104 is zirconium oxide represented by $ZrO_x$ in which the value of x is 1.4 or more, the resistive film 104 can stably change the resistance value. In such a case, the zirconium oxide film may have a thickness of 1 to 5 nm.

If the metal oxide constituting the resistive film 104 is tantalum oxide represented by $TaO_x$ in which the value of x is 2.1 or more, the resistive film 104 can stably change the resistance value.

The compositions of the above-mentioned metal oxide layers can be measured by Rutherford backscattering spectrometry.

The materials for the first electrode 103 and the second electrode 106 are selected from, for example, platinum (Pt), iridium (Ir), palladium (Pd), silver (Ag), nickel (Ni), tungsten (W), copper (Cu), aluminum (Al), tantalum (Ta), titanium (Ti), titanium nitride (TiN), tantalum nitride (TaN), and titanium aluminum nitride (TiAlN).

Specifically, the second electrode 106 is constituted of a material having a catalytic action of releasing hydrogen atoms from gas molecules containing hydrogen atoms, such as platinum (Pt), iridium (Ir), palladium (Pd), and alloys containing at least one thereof. The first electrode 103 may be constituted of a material having a standard electrode potential less than that of the metal constituting the metal oxide, such as tungsten (W), nickel (Ni), tantalum (Ta), titanium (Ti), aluminum (Al), tantalum nitride (TaN), and titanium nitride (TiN). A material having a higher standard electrode potential is more difficult to be oxidized.

The substrate 101 may be any substrate and is, for example, a silicon single crystal substrate or a semiconductor substrate. The resistive film 104 can be formed at a relatively low substrate temperature and can therefore be also formed on, for example, a resin material.

The gas sensor 100 may further include a load element electrically connected to the resistive film 104, such as a fixed resistance, a transistor, or a diode.

The characteristics of the gas sensor 100 of changing the resistance by voltage application will now be described based on the results of actual measurement using a sample device. The characteristics of the gas sensor 100 of changing the resistance by hydrogen-containing gas will be described below.

Figure 2:
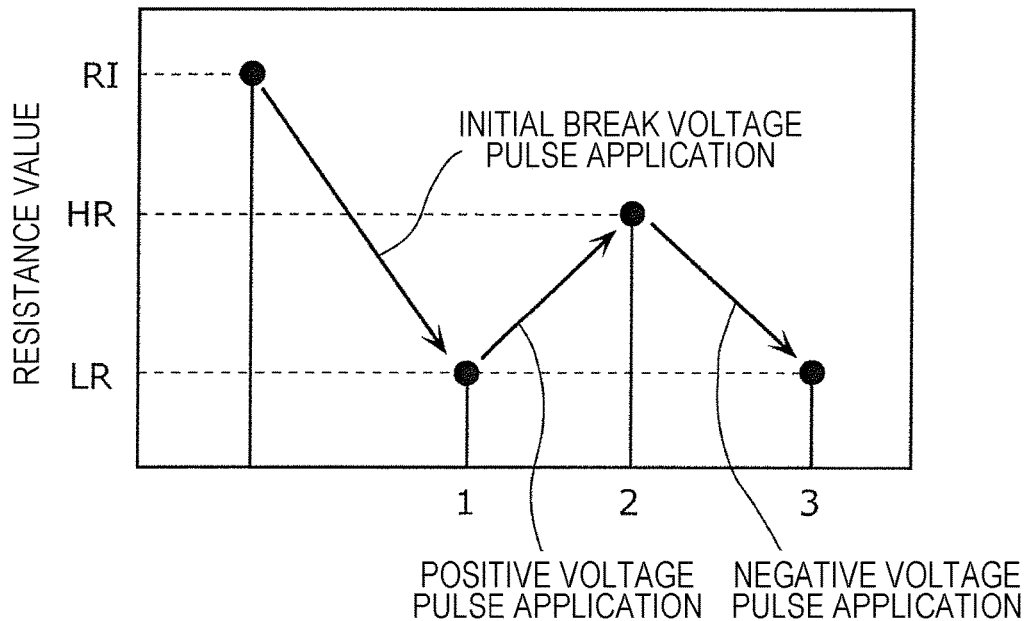
FIG. 2 is a diagram illustrating an example of the state transition of the gas sensor according to the embodiment.

FIG. 2 is a graph showing the resistance change characteristics actually measured using a sample device.

In the gas sensor 100 as the sample device giving the measurement results shown in FIG. 2, the first electrode 103, the second electrode 106, and the resistive film 104 each have a size of 0.5 μm×0.5 μm (area: 0.25 μm²); the value of y of TaOy representing the composition of tantalum oxide constituting the resistive film 104 is 2.47; and the resistive film 104 has a thickness of 5 nm. In such a gas sensor 100, if a read-out voltage (e.g., 0.4 V) is applied between the first electrode 103 and the second electrode 106, the initial resistance value RI is about $10^7$ to $10^8 \Omega$.

As shown in FIG. 2, if the resistance value of the gas sensor 100 is an initial resistance value RI (a value higher than the resistance value HR in the high resistive state), the resistive state changes by application of an initial break voltage between the first electrode 103 and the second electrode 106. Subsequently, as shown in FIG. 2, the resistance value between the first electrode 103 and the second electrode 106 changes by alternate application of, for example, two kinds of voltage pulses each having a pulse width of 100 ns and having different polarities (a positive voltage pulse and a negative voltage pulse), as a write-in voltage, between the first electrode 103 and the second electrode 106 of the gas sensor 100.

That is, application of a positive voltage pulse (pulse width: 100 ns) as the write-in voltage between the electrodes increases the resistance value between the first electrode 103 and the second electrode 106 from the low resistance value LR to the high resistance value HR. In contrast, application of a negative voltage pulse (pulse width: 100 ns) as the write-in voltage between the electrodes decreases the resistance value between the first electrode 103 and the second electrode 106 from the high resistance value HR to the low resistance value LR. The polarity of a voltage pulse is "positive" if the potential of the second electrode 106 is higher than that of the first electrode 103 as a reference and is "negative" if the potential of the second electrode 106 is less than that of the first electrode 103 as a reference.

Figure 3:
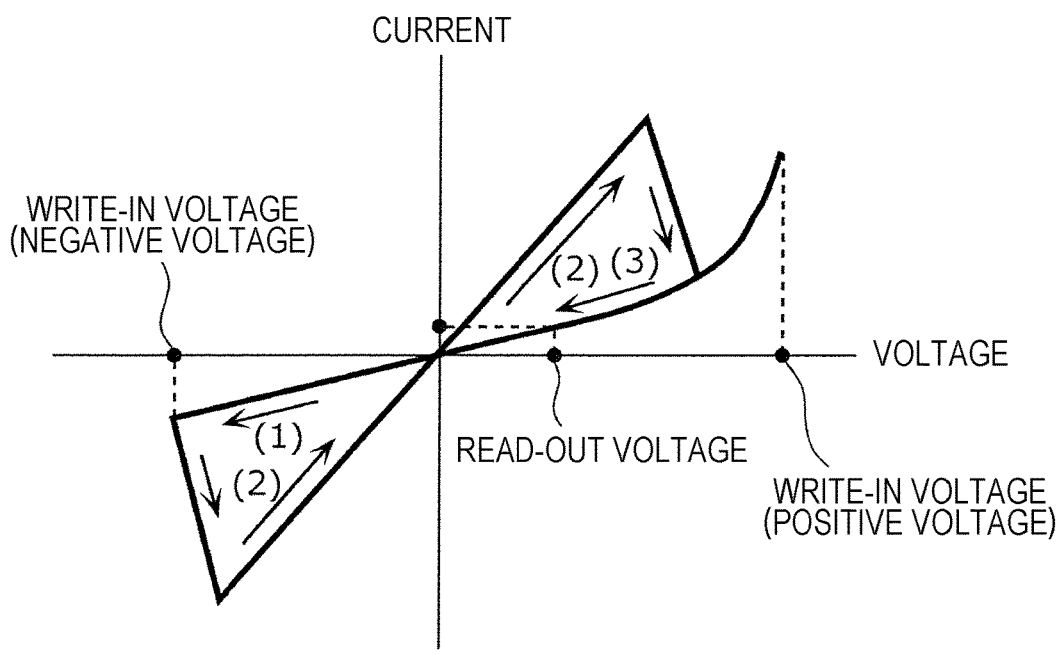
FIG. 3 is a diagram illustrating an example of the current-voltage characteristics of the gas sensor according to the embodiment.

FIG. 3 is a diagram illustrating an example of the current-voltage characteristics of the gas sensor 100. FIG. 3 shows the current-voltage characteristics obtained by measuring the current flowing in the gas sensor 100 while applying a varying voltage between the first electrode 103 and the second electrode 106 of the gas sensor 100. Specifically, the gas sensor 100 is set to a high resistive state in advance, and the applied voltage is (1) first changed from zero to a negative write-in voltage, (2) then changed from the negative write-in voltage to a positive write-in voltage, and (3) lastly changed from the positive write-in voltage to zero. Herein, the definitions of the positive and the negative of a voltage are as described above.

The resistance value between the first electrode 103 and the second electrode 106 decreases from the high resistance value HR to the low resistance value LR (the absolute value of current increases) when the applied voltage reached a predetermined negative voltage value. In contrast, the resistance value between the first electrode 103 and the second electrode 106 increases from the low resistance value LR to the high resistance value HR (the absolute value of current decreases) when the applied voltage reached a predetermined positive voltage value.

[Production Process of Gas Sensor and Operation Thereof]

An example of a process of producing the gas sensor 100 will now be described with reference to FIGS. 4A to 4G.

Figure 4A:
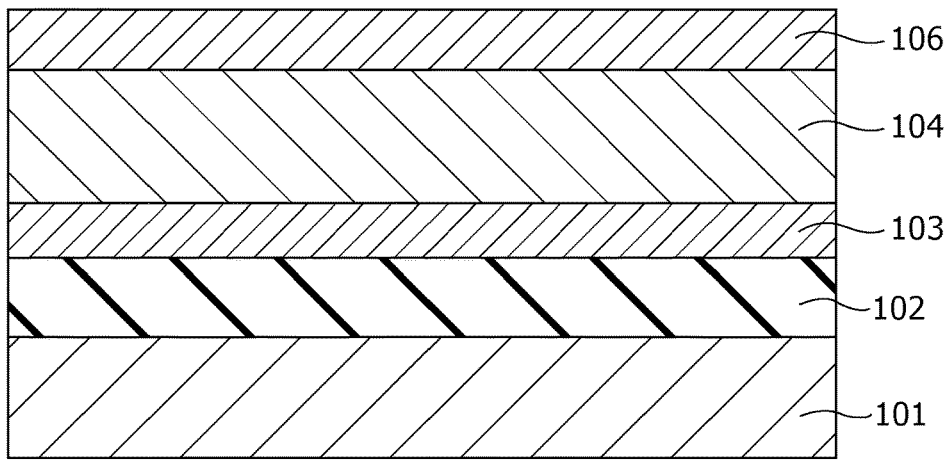
FIG. 4A is a cross-sectional view illustrating an example of a process of producing the gas sensor according to the embodiment.

First, as shown in FIG. 4A, an insulation film 102 having a thickness of 200 nm is formed on a substrate 101 of, for example, single crystal silicon by a thermal oxidation method. Subsequently, a first electrode 103 of, for example, a Pt thin film having a thickness of 100 nm is formed on the insulation film 102 by sputtering. In addition, an adhesion layer of, for example, Ti or TiN may be formed between the first electrode 103 and the insulation film 102 by sputtering. An oxygen-deficient metal oxide layer, which becomes a resistive film 104, is then formed on the first electrode 103 by reactive sputtering using, for example, a Ta target. A resistive film 104 is thus formed.

Herein, an excessively large thickness of the resistive film 104 causes disadvantages, such as a too high initial resistance value, and an excessively small thickness causes a disadvantage of not giving a stable change in resistance. Accordingly, the thickness may be about 1 nm or more and about 8 nm or less.

Subsequently, a second electrode 106 of, for example, a Pt thin film having a thickness of 150 nm is formed on the resistive film 104 by sputtering.

Figure 4B:
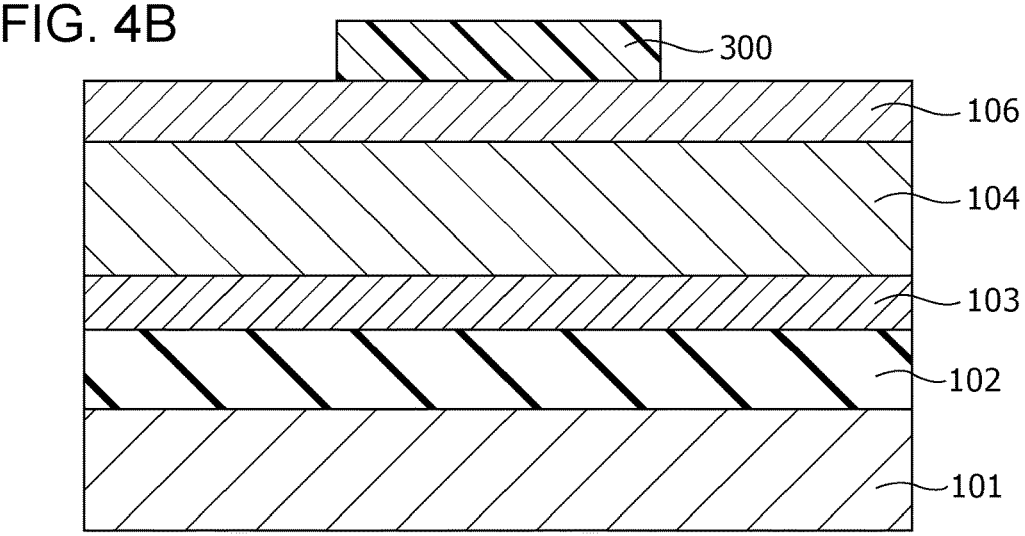
FIG. 4B is a cross-sectional view illustrating an example of the process of producing the gas sensor according to the embodiment.
Figure 4C:
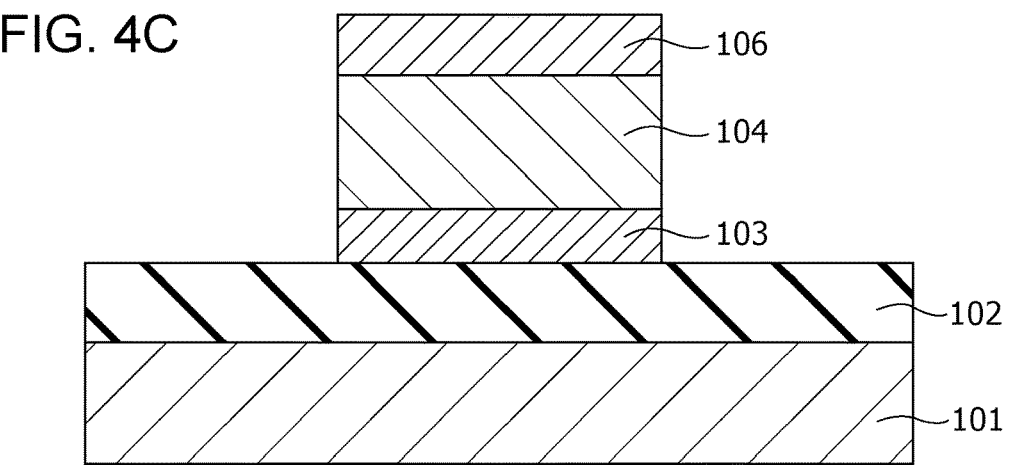
FIG. 4C is a cross-sectional view illustrating an example of the process of producing the gas sensor according to the embodiment.

Subsequently, as shown in FIG. 4B, a photoresist mask 300 is formed by a photolithography process. Then, as shown in FIG. 4C, the first electrode 103, the resistive film 104, and the second electrode 106 are formed into the shape of the device by dry etching using the mask 300.

Figure 4D:
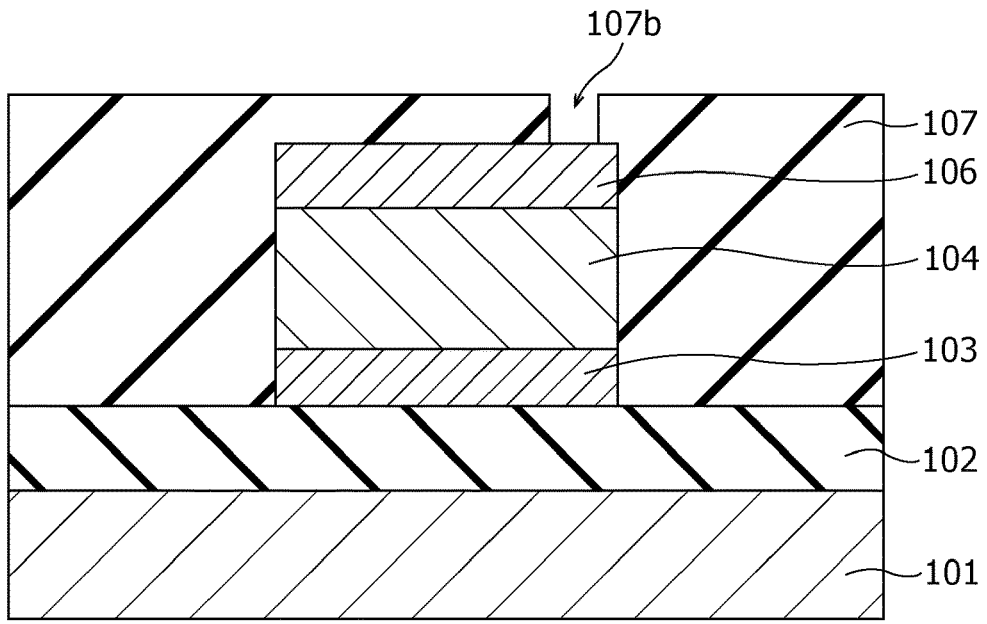
FIG. 4D is a cross-sectional view illustrating an example of the process of producing the gas sensor according to the embodiment.

Then, as shown in FIG. 4D, an insulation film 107 is formed so as to cover the insulation film 102, the first electrode 103, the resistive film 104, and the second electrode 106. The insulation film 107 is then etched to form a via hole 107b reaching a part of the upper surface of the second electrode 106.

Figure 4E:
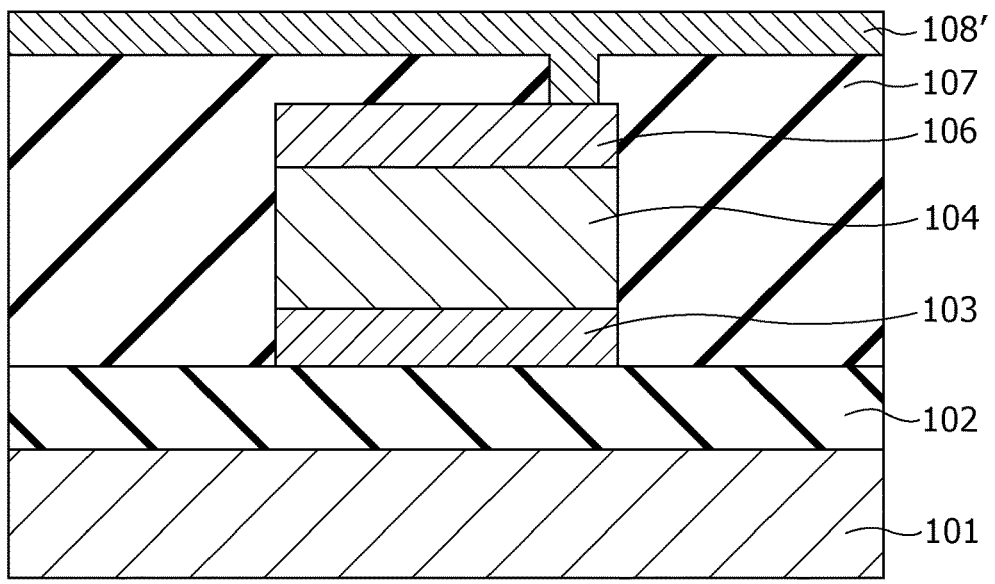
FIG. 4E is a cross-sectional view illustrating an example of the process of producing the gas sensor according to the embodiment.
Figure 4F:
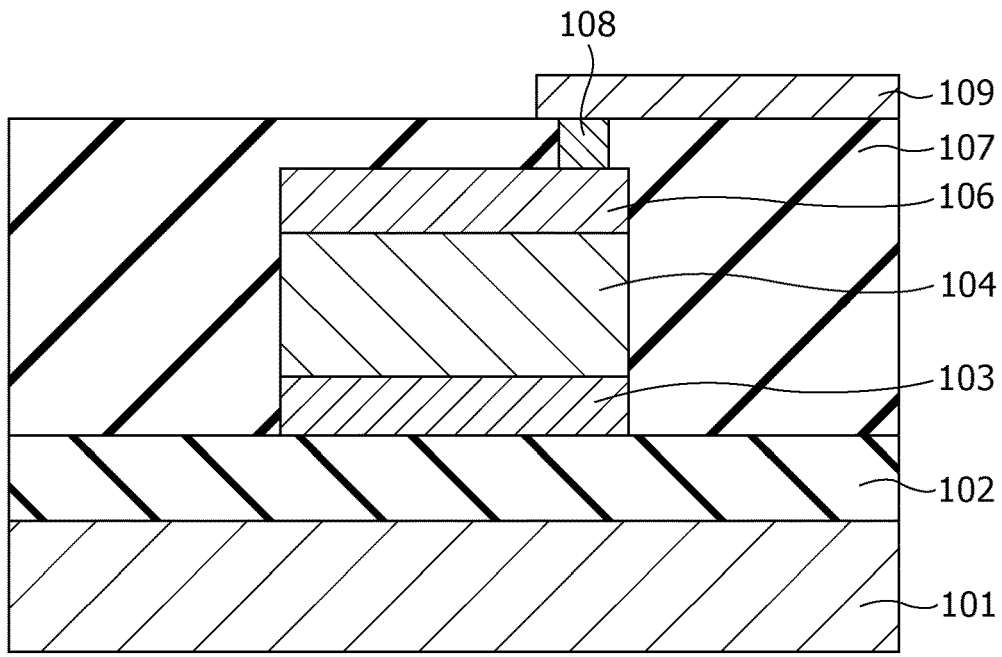
FIG. 4F is a cross-sectional view illustrating an example of the process of producing the gas sensor according to the embodiment.

Subsequently, as shown in FIG. 4E, a conductor film 108' is formed on the upper surface of the insulation film 107 and the inside of the via hole 107b so as to fill the via hole 107b. Then, as shown in FIG. 4F, the conductor film 108' on the insulation film 107 is removed by chemical mechanical polishing (CMP) to form a via 108 in the via hole 107b. Another conductor film is further formed on the insulation film 107 and is patterned to form a wiring 109 connected to the via 108.

Figure 4G:
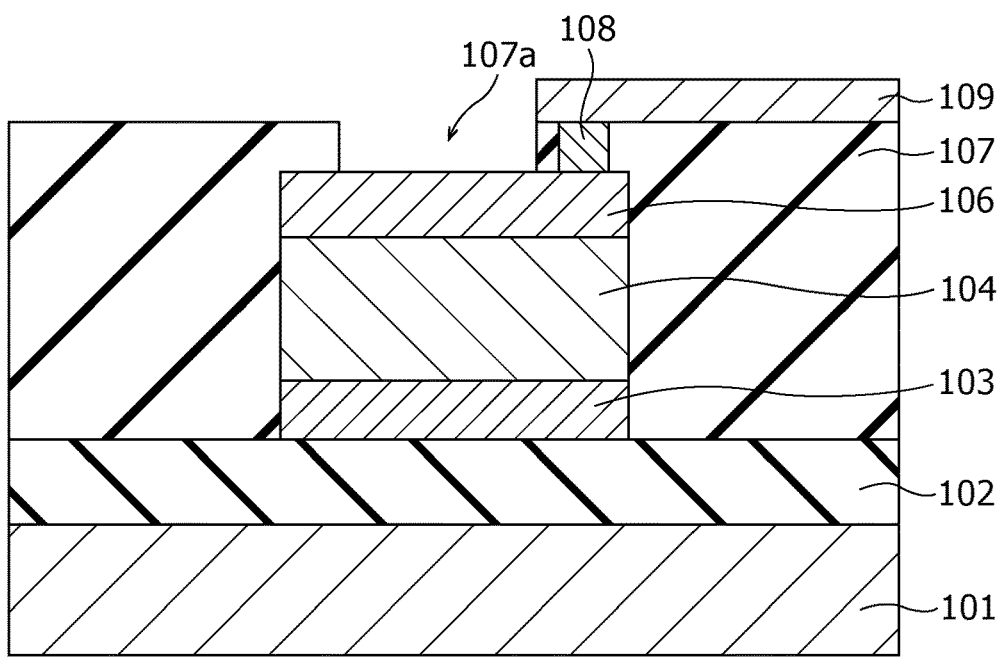
FIG. 4G is a cross-sectional view illustrating an example of the process of producing the gas sensor according to the embodiment.

Subsequently, as shown in FIG. 4G, the insulation film 107 is etched to form an opening 107a exposing a part of the upper surface of the second electrode 106.

Subsequently, an initial break voltage is applied between the first electrode 103 and the second electrode 106 to form a local area 105 shown in FIG. 1A in the resistive film 104. A gas sensor 100 is thus produced.

[Modification of Gas Sensor]

Figure 5:
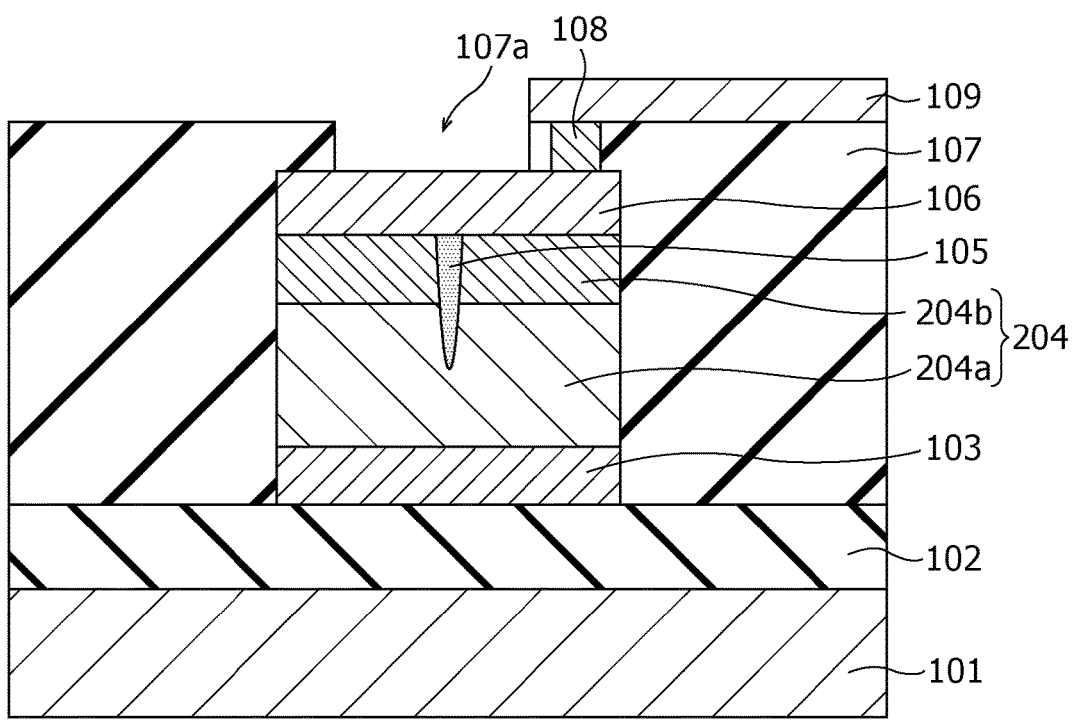
FIG. 5 is a cross-sectional view of a gas sensor according to a modification of the embodiment.

FIG. 5 is a cross-sectional view illustrating an example of the structure of a gas sensor according to a modification of First Embodiment. Only the points different from the gas sensor 100 of First Embodiment will now be described.

The gas sensor 200 of the modification differs from the gas sensor 100 of First Embodiment in that the resistive film 204 is a laminate of a first metal oxide layer 204a being in contact with the first electrode 103 and a second metal oxide layer 204b being in contact with the second electrode 106. The resistive film 204 is not limited to a laminate of two layers and may be a laminate of three or more layers.

The first metal oxide layer 204a and the second metal oxide layer 204b include a local area 105 that reversibly changes the degree of oxygen deficiency depending on application of an electric pulse and hydrogen-containing gas. The local area 105 at least passes through the second metal oxide layer 204b and is in contact with the second electrode 106.

In other words, the resistive film 204 includes a layered structure at least composed of a first metal oxide layer 204a containing a first metal oxide and a second metal oxide layer 204b containing a second metal oxide. The first metal oxide layer 204a is disposed between the first electrode 103 and the second metal oxide layer 204b, and the second metal oxide layer 204b is disposed between the first metal oxide layer 204a and the second electrode 106.

The second metal oxide layer 204b may have a thickness smaller than that of the first metal oxide layer 204a. In such a case, a structure including the local area 105 not being in contact with the first electrode 103 can be readily formed. The second metal oxide layer 204b may have a degree of oxygen deficiency less than that of the first metal oxide layer 204a. In such a case, the resistance value of the second metal oxide layer 204b is higher than that of the first metal oxide layer 204a. Accordingly, most of the voltage applied to the resistive film 204 is applied to the second metal oxide layer 204b. This structure is useful for, for example, concentrating the initial break voltage in the second metal oxide layer 204b and reducing the initial break voltage necessary for forming the local area 105.

In the present disclosure, if the metals constituting the first metal oxide layer 204a and the second metal oxide layer 204b are the same, the term "oxygen content" may be used instead of the term "degree of oxygen deficiency". A "high oxygen content" corresponds to a "low degree of oxygen deficiency", and a "low oxygen content" corresponds to a "high degree of oxygen deficiency".

However, as described below, the resistive film 204 according to this embodiment is not limited to the case that the metals constituting the first metal oxide layer 204a and the second metal oxide layer 204b are the same, and the metals may be different from each other. That is, the first metal oxide layer 204a and the second metal oxide layer 204b may be made of different metal oxides.

If the first metal constituting the first metal oxide layer 204a and the second metal constituting the second metal oxide layer 204b are the same, the oxygen content has a corresponding relationship with the degree of oxygen deficiency. That is, if the oxygen content of the second metal oxide is higher than that of the first metal oxide, the second metal oxide has a degree of oxygen deficiency less than that of the first metal oxide.

The resistive film 204 includes a local area 105 in the vicinity of the interface between the first metal oxide layer 204a and the second metal oxide layer 204b. The local area 105 has a degree of oxygen deficiency higher than that of the second metal oxide layer 204b and is different from that of the first metal oxide layer 204a.

The local area 105 is formed in the resistive film 204 by applying an initial break voltage between the first electrode 103 and the second electrode 106. The initial break voltage forms the local area 105 being in contact with the second electrode 106, passing through the second metal oxide layer 204b, partially penetrating into the first metal oxide layer 204a, and being not in contact with the first electrode 103.

An example of evaluating the characteristics of the thus-structured gas sensor 200 of changing the resistance by hydrogen-containing gas will now be described.

Figure 6:
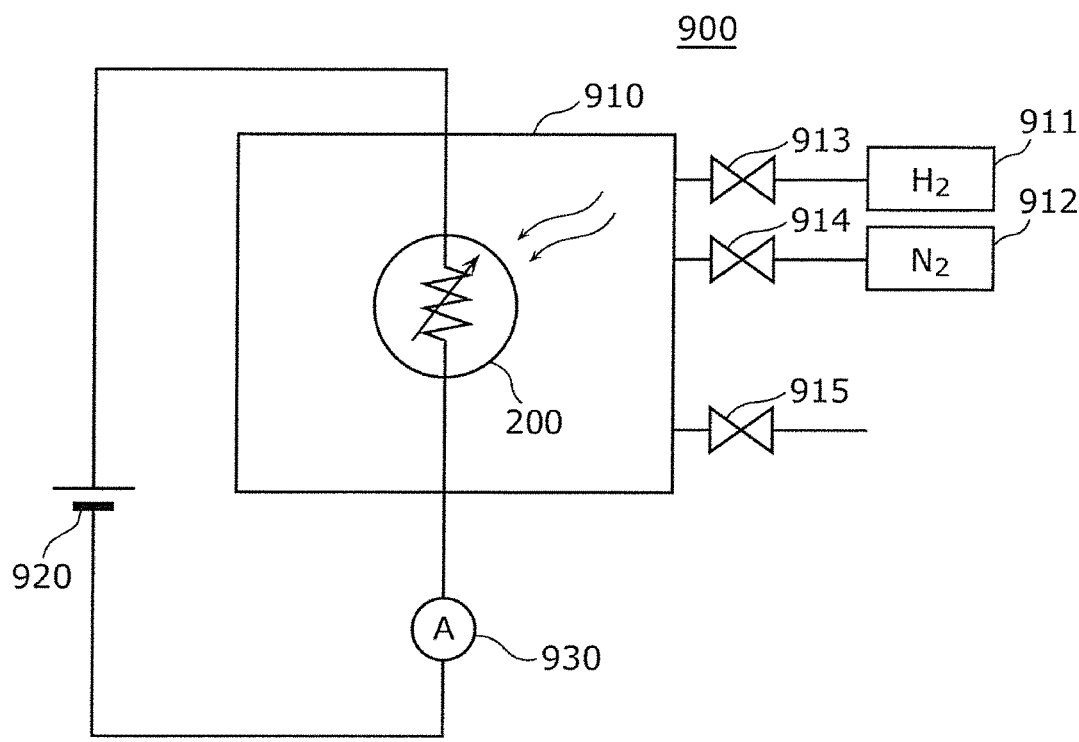
FIG. 6 is a diagram illustrating an evaluation system of the gas sensor according to the modification of the embodiment.

FIG. 6 is a block diagram illustrating an example of an evaluation system used for evaluating the gas sensor 200. The evaluation system 900 shown in FIG. 6 includes an airtight container 910 accommodating the gas sensor 200, a detection power supply 920 generating a detection voltage, and a current meter 930. The airtight container 910 is connected to a hydrogen cylinder 911 and a nitrogen cylinder 912 through introduction valves 913 and 914, respectively, and is configured such that the gas in the inside can be exhausted through an exhaust valve 915.

Figure 7:
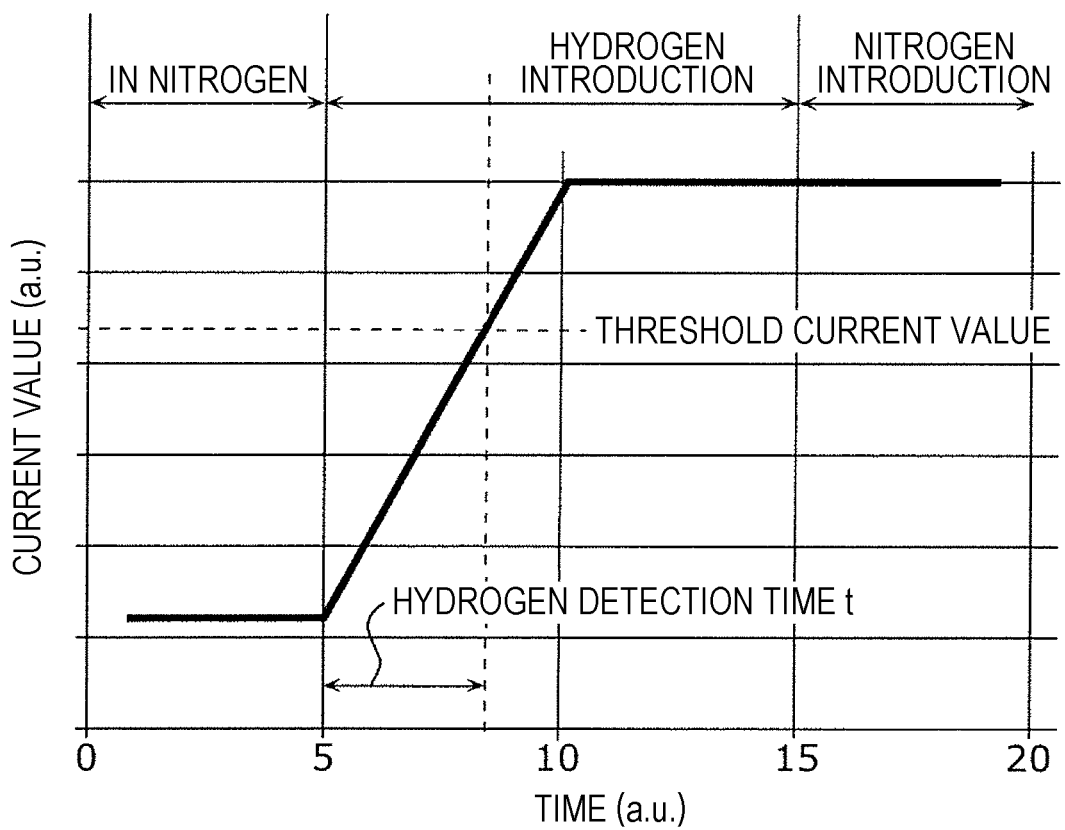
FIG. 7 is a diagram illustrating the results of evaluation of the gas sensor according to the modification of the embodiment.

FIG. 7 is a graph showing an example of evaluation of the gas sensor 200. The horizontal axis indicates the time (arbitrary unit: a.u.), and the vertical axis indicates the value (a.u.) of current flowing in the gas sensor 200. In the experiment, the gas sensor 200 was placed in the nitrogen gas introduced into the airtight container 910, and the measurement of current was started by application of a detection voltage. Subsequently, hydrogen gas was introduced into the airtight container 910. After passage of a predetermined period of time, the introduction gas was changed from hydrogen gas to nitrogen gas.

FIG. 7 shows the results of the above experiment. The horizontal axis indicates the three periods of in nitrogen, introduction of hydrogen, and introduction of nitrogen. The current value starts to increase after the start of introduction of hydrogen gas, and the hydrogen gas is detected by that the current value reaches a predetermined threshold current value. The time for increasing the current value from that at the start of introduction of hydrogen gas to the predetermined threshold current value is represented by hydrogen detection time t. After the detection of hydrogen, the current value further increases to saturation.

After the detection of hydrogen gas, even if the introduction gas was changed from hydrogen gas to nitrogen gas, the current value was remained to be saturated and did not decrease again. That is, it can be perceived that the gas sensor 200 has characteristics of decreasing the resistance value between the first electrode 103 and the second electrode 106 by the contact of the second electrode 106 with gas containing hydrogen molecules containing hydrogen atoms (herein, hydrogen gas) and of maintaining the reduced resistance value even if the second electrode 106 is then brought into contact with gas not containing hydrogen atoms (herein, nitrogen gas).

In this example of evaluation, the gas sensor 200 was used after application of a predetermined voltage (reset voltage) between the first electrode 103 and the second electrode 106 to previously set the local area 105 to a high resistive state.

In the monitoring behavior for hydrogen-containing gas, a detection voltage of 0.6 V was applied between the first electrode 103 and the second electrode 106 to detect hydrogen gas, and in the state that the current value was saturated, a current of about 20 µA flowed between the first electrode 103 and the second electrode 106.

It is therefore demonstrated that the gas sensor 200 can monitor hydrogen-containing gas with a very small power consumption of 0.012 mW at the highest. This voltage of 0.6 V may be applied at all times between the first electrode 103 and the second electrode 106.

In the case of applying a detection voltage of 0.4 V between the first electrode 103 and the second electrode 106, a change in resistance by hydrogen gas was not caused, and the hydrogen gas could not be detected. This was probably caused by that the heat generation in the local area 105 by application of a detection voltage of 0.4 V was insufficient for accelerating the catalytic action of the second electrode 106 and application of a detection voltage of 0.6 V is necessary for enabling the detection of hydrogen gas. The detection voltage of 0.6 V in this case is an example of the detection voltage for activating the characteristics of decreasing the resistance value between the first electrode 103 and the second electrode 106 by the contact of the second electrode 106 with gas including gas molecules containing hydrogen atoms.

Herein, the detection voltage is a read-out voltage shown in FIG. 3. The resistance value of the gas sensor 200 must be prevented from changing excluding changes caused by hydrogen atoms. As shown in FIG. 3, application of a positive voltage having a predetermined level to the gas sensor 200 changes the resistance value of the gas sensor 200 from a low resistance to a high resistance, and application of a negative voltage having a predetermined level changes the resistance value of the gas sensor 200 from a high resistance to a low resistance. Accordingly, the absolute value of the detection voltage (read-out voltage) must be lower than a predetermined value for preventing occurrence of a change in the resistance value.

In the gas sensor 200, after the detection of hydrogen gas and an increase in the current value to saturation, the current value does not decrease again even if the concentration of hydrogen gas is decreased. Accordingly, in order to return the gas sensor 200 to the same high resistive state as that before the detection of hydrogen gas, it is necessary to apply a positive voltage (reset voltage) having the predetermined level between the first electrode 103 and the second electrode 106 again.

From the results described above, the inventors presume the mechanism of detecting hydrogen-containing gas with the gas sensor 200 as follows.

The contact of the second electrode 106 with hydrogen-containing gas causes a release of hydrogen atoms from the hydrogen-containing gas by the catalytic action of the second electrode 106. The released hydrogen atoms diffuse in the second electrode 106 for maintaining the equilibrium state and reach the local area 105.

It is inferred that the hydrogen atoms reached the local area 105 cause a redox reaction in the minute local area 105 and react with oxygen in the local area 105 to newly generate oxygen defects in the local area 105 and increase the degree of oxygen deficiency in the local area 105; the generation of a large number of oxygen defects in the local area 105 allows the filaments formed from the oxygen defects to be readily connected to one another to reduce the resistance value of the local area 105; and as a result, the current flowing between the first electrode 103 and the second electrode 106 is increased.

It is inferred that the above-described behavior is not limited to the gas sensor 200 and also occurs in the gas sensor 100 or another gas sensor having substantially the same main structure as that of the gas sensor 200. It is also inferred that the above-described behavior is not limited to detection of hydrogen gas and occurs in a variety of hydrogen-containing gases, such as methane and alcohol.

As described above, the gas sensor according to the embodiment can generate heat by only the current for detecting the resistive state and can detect hydrogen-containing gas without heating with a separate heater. Thus, a gas sensor having excellent power-saving properties can be given.

In addition, the contact of the second electrode with gas including gas molecules containing hydrogen atoms decreases the resistance value between the first electrode and the second electrode, and the reduced resistance value can be maintained even if the second electrode is then brought into contact with gas not containing hydrogen atoms.

[Gas Detection Circuit]

Figure 8A:
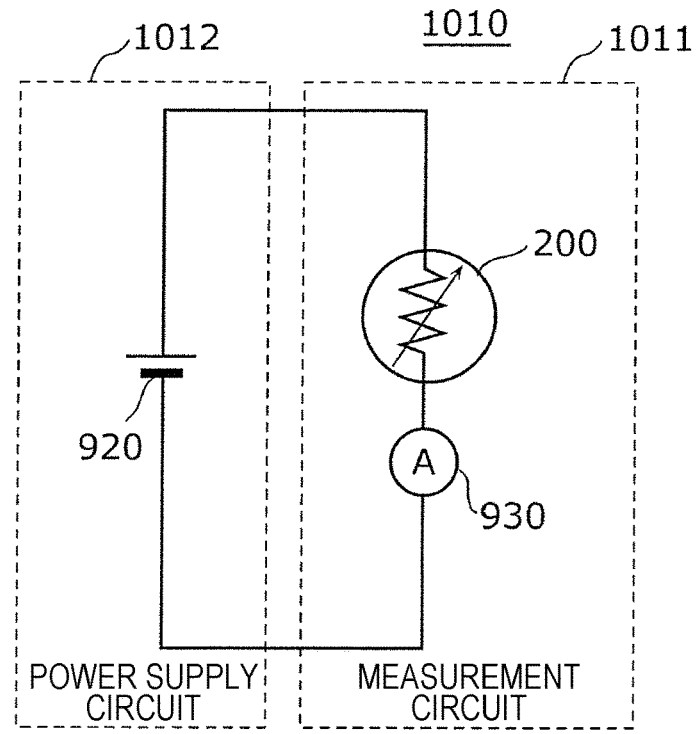
FIG. 8A is a circuit diagram illustrating an example of a gas detection circuit according to an embodiment.

FIG. 8A is a circuit diagram illustrating an example of a gas detection circuit 1010 including the gas sensor 200 according to the modification of First Embodiment.

The gas detection circuit 1010 includes a measurement circuit 1011 composed of the gas sensor 200 and a current meter 930 connected in series and a power supply circuit 1012 including a detection power supply 920.

More specifically, the second electrode 106 of the gas sensor 200 is connected to the plus potential terminal of the detection power supply 920 through the via 108 and the wiring 109 shown in FIG. 5. The first electrode 103 of the gas sensor 200 is connected to one end of the current meter 930 through, for example, a wiring (not shown). The other end of the current meter 930 is connected to the minus potential terminal of the detection power supply 920. In this structure, the detection power supply 920 applies a predetermined voltage between the first electrode 103 and the second electrode 106 of the gas sensor 200.

The gas detection circuit 1010 determines the time at which the current exceeds a predetermined threshold current value shown in FIG. 7 after the start of introduction of hydrogen gas as the point of judging the hydrogen detection in the current meter 930 connected to the gas sensor 200. That is, the gas detection circuit 1010 judges that the gas sensor 200 has detected hydrogen at the time at which the current exceeds a predetermined threshold current value.

As described above, the gas sensor of the embodiment can detect hydrogen with reduced power consumption. Although the experimental results in hydrogen gas have been described in the embodiment, the same advantageous effects were also observed in gas containing hydrogen (e.g., ammonium gas).

Although the example described above is of detecting hydrogen, the gas sensor of the embodiment not only detects hydrogen but also has characteristics of retaining the state of hydrogen detection (maintaining the high resistive state even if the hydrogen concentration decreased). Accordingly, the gas sensor according to the embodiment can also be effectively used as a hydrogen-leakage memory device for investigating whether leakage of hydrogen occurred in the past or not by installing a plurality of the gas sensors in, for example, a hydrogen plant.

[Gas Detection Circuit Having Reset Function]

Figure 8B:
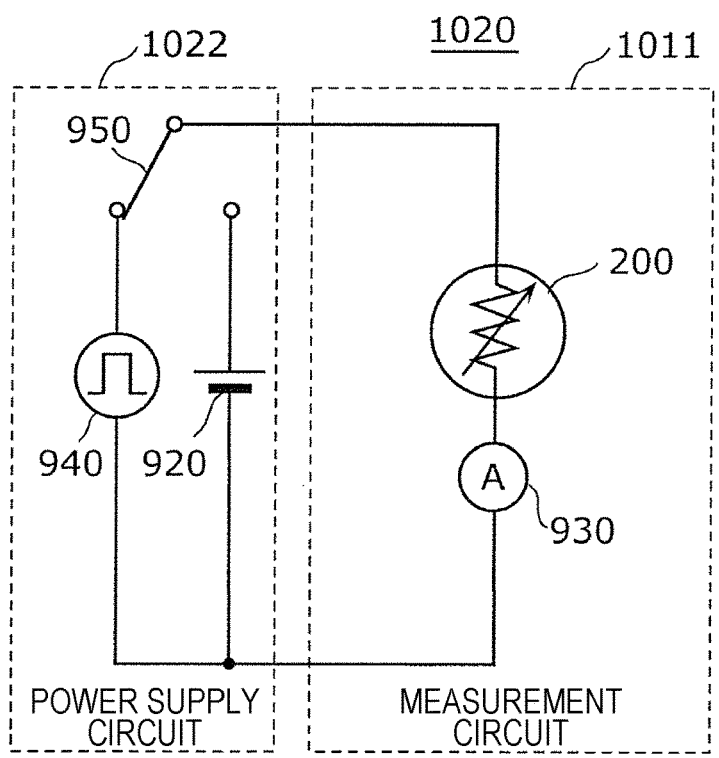
FIG. 8B is a circuit diagram illustrating an example of another gas detection circuit according to an embodiment.

FIG. 8B is a circuit diagram illustrating an example of a gas detection circuit that can reset the gas sensor 200 from the low resistive state to the high resistive state. In the gas detection circuit 1020 shown in FIG. 8B, the power supply circuit 1012 of the gas detection circuit 1010 shown in FIG. 8A is changed to a power supply circuit 1022 further including a changeover switch 950 and reset power supply 940.

The gas detection circuit 1020 uses the gas sensor 200 and the current meter 930 for detecting hydrogen-containing gas and then connects the changeover switch 950 to the reset power supply 940. The reset power supply 940 applies a reset voltage (e.g., 1.5 V) to the gas sensor 200 to electrically reset the gas sensor 200 in the low resistive state due to the hydrogen-containing gas to the high resistive state.

Accordingly, it is possible to repeatedly detect hydrogen-containing gas by resetting the gas sensor 200 in the low resistive state after the detection of hydrogen-containing gas to the high resistive state.

The advantageous effects of the gas detection circuits 1010 and 1020 described above are not limited to the gas detection circuits 1010 and 1020 including the gas sensor 200. The same effects can be obtained even if the gas sensor 100 or another gas sensor having substantially the same main structure as that of the gas sensor 200 is used instead of the gas sensor 200.

The timing of resetting the gas sensor to the high resistive state by applying a reset voltage between the first electrode and the second electrode is not limited to the time after the detection of hydrogen-containing gas. For example, the gas sensor may also be reset before the detection of hydrogen-containing gas (in particular, before the first detection). As a result, a reduction in the resistance value can be more clearly detected by detecting hydrogen-containing gas with a gas sensor in a high resistive state. Thus, the hydrogen-containing gas detection characteristics are improved.

[Supplement]

As shown in FIG. 8A, the gas detection circuit 1010 includes a measurement circuit 1011 including the gas sensor 200 and a current meter 930 and includes a power supply circuit 1012. The gas detection circuit 1010 is an example of the "gas-detecting apparatus" in the present disclosure.

As shown in FIG. 5, the gas sensor 200 includes a first electrode 103, a resistive film disposed on the first electrode 103, and a second electrode 106 disposed on the resistive film 204. The resistive film 204 is an example of the "metal oxide layer" of the present disclosure. The resistive film 204 includes a first metal oxide layer 204a and a second metal oxide layer 204b. The resistive film 204 includes a local area 105 and a bulk area surrounding the local area 105. Herein, the term "surrounding the local area 105" is not limited to entirely surrounding the outer periphery of the local area 105. In FIG. 5, the bulk area is the region of the second metal oxide layer 204b excluding the local area 105. The local area 105 has a degree of oxygen deficiency higher than that of the bulk area. The first metal oxide layer 204a has a degree of oxygen deficiency higher than that of the bulk area. In FIG. 5, the local area 105 is in contact with the second electrode 106, passes through the second metal oxide layer 204b, and is not in contact with the first electrode 103.

In FIG. 5, the insulation film 107 includes an opening 107a. In the opening 107a, a part of the upper surface of the second electrode 106 is exposed from the insulation film 107. The exposed surface of the second electrode 106 is allowed to come into contact with gas.

The contact of the second electrode 106 with gas containing hydrogen atoms decreases the resistance value of the local area 105, decreases the resistance value of the resistive film 204; and decreases the resistance value of the gas sensor 200.

The power supply circuit 101 applies a predetermined voltage, for example, between the first electrode 103 and the second electrode 106 before a reduction in the resistance value of the resistive film 204 to increase the resistance value of the resistive film 204. For example, the resistive film 204 is set to a high resistive state by the voltage and then transitions to a low resistive state by hydrogen-containing gas. Alternatively, the power supply circuit 1012 applies a predetermined voltage, for example, between the first electrode 103 and the second electrode 106 after a reduction in the resistance value of the resistive film 204 to increase the resistance value of the resistive film 204. For example, the resistive film 204 transitions to a low resistive state by hydrogen-containing gas and is then set to a high resistive state by the voltage. Alternatively, the resistive film 204 is set to a high resistive state by a voltage, then transits to a low resistive state by hydrogen-containing gas, and may be further reset to a high resistive state by a voltage.

In FIG. 8B, the reset power supply 940 is an example of the "first power supply circuit" in the present disclosure, and the detection power supply 920 is an example of the "second power supply circuit" in the present disclosure. The "power supply circuit" in the present disclosure, for example, may be a power supply itself or may be a conversion circuit for converting the voltage of an external power supply to a desired voltage.

Overviews of Embodiments

A gas sensor according to an aspect includes first and second electrodes disposed such that main surfaces thereof face each other; a metal oxide layer disposed so as to be in contact with the main surface of the first electrode and the main surface of the second electrode; a local area disposed in the inside of the metal oxide layer so as to be in contact with the second electrode and having a degree of oxygen deficiency higher than that of the metal oxide layer; and an insulation film covering the first electrode, the second electrode, and the metal oxide layer, wherein at least a part of the other surface opposite to the main surface of the second electrode is exposed without being covered with the insulation film. The gas sensor has characteristics of decreasing the resistance value between the first electrode and the second electrode by the contact of the second electrode with gas including gas molecules containing hydrogen atoms and of maintaining the reduced resistance value even if the second electrode is brought into contact with gas not containing hydrogen atoms after the decrease.

In such a structure, the current flowing between the first electrode and the second electrode is concentrated in the local area having a high degree of oxygen deficiency. As a result, the temperature of the local area can be increased with a small amount of current.

The local area generates heat by the current flowing between the first electrode and the second electrode; hydrogen atoms are thereby released from the hydrogen molecules in the portion of the second electrode being in contact with the local area; and the released hydrogen atoms bind to oxygen atoms in the local area of the metal oxide layer to reduce the resistance value between the first electrode and the second electrode.

More specifically, an increase in the temperature of the local area increases the temperature of the surface of the second electrode. This increase in the temperature enhances the efficiency of releasing hydrogen atoms from hydrogen molecules at the second electrode by the catalytic action of the second electrode.

The contact of hydrogen molecules passed through the insulation film with the second electrode releases hydrogen atoms from the hydrogen molecules. The released hydrogen atoms diffuse in the second electrode and reach the local area. The hydrogen atoms then bind to oxygen of the metal oxide present in the local area into water ($H_2O$). Consequently, the degree of oxygen deficiency of the local area is further increased. As a result, current easily flows in the local area, and the resistance between the first electrode and the second electrode decreases.

Consequently, the resulting gas sensor can detect hydrogen-containing gas utilizing the self-heating and gas sensitivity of the local area formed in the inside of the metal oxide layer without heating with a heater and thus has excellent power-saving properties.

In addition, the resulting gas sensor stores the detection results by utilizing the characteristics of maintaining the resistance value reduced by the detection of hydrogen-containing gas.

The metal oxide layer is a laminate composed of a first metal oxide layer made of a first metal oxide and a second metal oxide layer made of a second metal oxide having a degree of oxygen deficiency less than that of the first metal oxide. The first metal oxide layer is in contact with the first electrode, and the second metal oxide layer is in contact with the second electrode. The local area is formed so as to at least pass through the second metal oxide layer and be in contact with the second electrode and may have a degree of oxygen deficiency higher than that of the second metal oxide layer.

In such a structure, the employment of the layered structure having excellent resistance change characteristics as the metal oxide layer can provide a gas sensor having excellent characteristics of detecting hydrogen-containing gas.

The second electrode may be made of a material having a catalytic action for releasing hydrogen atoms from the gas molecules.

In such a structure, hydrogen atoms are released from the hydrogen molecules in the portion of the second electrode being in contact with the local area. The released hydrogen atoms bind to oxygen atoms in the local area of the metal oxide layer to reduce the resistance value between the first electrode and the second electrode.

The second electrode may be made of platinum, palladium, iridium, or an alloy containing at least one of platinum, palladium, and iridium.

In such a structure, the second electrode can release hydrogen atoms from the hydrogen molecules by the catalytic action of platinum or palladium.

The gas sensor may include a measurement circuit for measuring the current flowing between the first electrode and the second electrode when a detection voltage is applied between the first electrode and the second electrode.

Such a structure can detect the hydrogen-containing gas through an increase in the current measured with the current meter.

The metal oxide layer may reversibly transition between a high resistive state and a low resistive state having a resistance value less than that of the high resistive state based on the voltage applied between the first electrode and the second electrode.

In such a structure, transition of the resistive state of the metal oxide layer can be electrically performed, in addition to the transition by hydrogen-containing gas. For example, the gas as an object to be tested may be brought into contact with the metal oxide layer after electrically setting the metal oxide layer to a high resistive state. In such a case, a reduction in the resistance value can be clearly detected to enhance the characteristics of detecting hydrogen-containing gas.

The metal oxide layer may be set to a high resistive state before bringing gas including gas molecules containing hydrogen atoms into contact with the second electrode by applying a reset voltage between the first electrode and the second electrode.

In such a structure, since a reduction in the resistance value of the metal oxide layer electrically set to a high resistive state is detected, the reduction in the resistance value can be clearly detected to enhance the characteristics of detecting hydrogen-containing gas.

The metal oxide layer may be set to a high resistive state by applying the reset voltage between the first electrode and the second electrode again after the second electrode comes into contact with gas including gas molecules containing hydrogen atoms and the resistance value between the first electrode and the second electrode is decreased.

In such a structure, even if the metal oxide layer is maintained at a low resistive state after the detection of hydrogen-containing gas, it is possible to detect hydrogen-containing gas again by electrical reset to a high resistive state.

The gas sensor may include a power supply circuit including a detection power supply generating a detection voltage for measuring the current flowing between the first electrode and the second electrode, a reset power supply generating a reset voltage for setting the metal oxide layer to a high resistive state, and a changeover switch for switching the detection power supply and the reset power supply to selectively applying any one of the detection voltage and the reset voltage between the first electrode and the second electrode.

In such a structure, the gas sensor can have high convenience as a module component including power supplies for current measurement and giving high resistance (reset).

The absolute value of the detection voltage may be less than that of the reset voltage.

In such a structure, the gas sensor can have excellent power-saving properties by applying minimum voltages suitable for current measurement and giving high resistance (reset) between the first electrode and the second electrode.

The gas sensor may include a power supply circuit for applying a voltage, for activating the characteristics of decreasing the resistance value between the first electrode and the second electrode by the contact of the second electrode with gas including gas molecules containing hydrogen atoms, at all times between the first electrode and the second electrode.

In such a structure, it is possible to continuously monitor leakage of hydrogen-containing gas with a slight power by utilizing the power-saving properties of the gas sensor.

The metal oxide layer may be made of a transition metal oxide or an aluminum oxide.

In such a structure, the gas sensor can have excellent characteristics of detecting hydrogen-containing gas by forming the metal oxide layer from a transition metal oxide or an aluminum oxide having excellent resistance change characteristics.

The transition metal oxide may be any of tantalum oxide, hafnium oxide, and zirconium oxide.

In such a structure, the gas sensor can have excellent characteristics of detecting hydrogen-containing gas by using tantalum oxide, hafnium oxide, or zirconium oxide having excellent resistance change characteristics as the transition metal oxide.

The local area generates heat by the current flowing between the first electrode and the second electrode; hydrogen atoms are thereby released from the gas molecules in the portion of the second electrode being in contact with the local area; and the released hydrogen atoms bind to oxygen atoms in the local area of the metal oxide layer. The resistance value between the first electrode and the second electrode may be thus reduced.

In such a structure, the current flowing between the first electrode and the second electrode is concentrated in the local area having a high degree of oxygen deficiency. As a result, the temperature of the local area can be increased with a small amount of current.

The local area generates heat by the current flowing between the first electrode and the second electrode; hydrogen atoms are thereby released from the hydrogen molecules in the portion of the second electrode being in contact with the local area; and the released hydrogen atoms bind to oxygen atoms in the local area of the metal oxide layer to reduce the resistance value between the first electrode and the second electrode.

More specifically, an increase in the temperature of the local area increases the temperature of the surface of the second electrode. This increase in the temperature enhances the efficiency of releasing hydrogen atoms from gas molecules containing hydrogen atoms at the second electrode by the catalytic action of the second electrode.

The contact of gas molecules containing hydrogen atoms passed through the insulation film with the second electrode releases hydrogen atoms from the gas molecules. The released hydrogen atoms diffuse in the second electrode and reach the local area. The hydrogen atoms then bind to oxygen of the metal oxide present in the local area into water. Consequently, the degree of oxygen deficiency of the local area is further increased. As a result, current easily flows in the local area, and the resistance between the first electrode and the second electrode decreases.

Consequently, the resulting gas sensor can detect hydrogen-containing gas utilizing the self-heating and gas sensitivity of the local area formed in the inside of the metal oxide layer without heating with a heater and thus has excellent power-saving properties.

The method of detecting hydrogen according to an aspect uses a gas sensor that includes first and second electrodes disposed such that main surfaces thereof face each other and a metal oxide layer disposed so as to be in contact with the main surface of the first electrode and the main surface of the second electrode and has characteristics of decreasing the resistance value between the first electrode and the second electrode by the contact of the second electrode with gas including gas molecules containing hydrogen atoms and of maintaining the reduced resistance value even if the second electrode after the reduction is brought into contact with gas not containing hydrogen atoms. The method includes bringing gas including gas molecules containing hydrogen atoms into contact with the second electrode to reduce the resistance value between the first electrode and the second electrode; detecting the gas molecules containing hydrogen atoms through the reduction; and after the reduction of resistance value between the first electrode and the second electrode by the gas molecules containing hydrogen atoms, applying a reset voltage between the first electrode and the second electrode to reset the resistance value between the first electrode and the second electrode to the same high resistance value as that before the reduction.

In such a method, hydrogen can be detected with excellent power-saving properties with the gas sensor generating heat by only the current for detecting the resistive state and detecting hydrogen-containing gas without heating with a separate heater.

In addition, even if the metal oxide layer is maintained at a low resistive state after the detection of hydrogen-containing gas, it is possible to detect hydrogen-containing gas again by electrical reset to a high resistive state.

The gas-detecting apparatus according to the present disclosure is useful for, for example, fuel-cell vehicles, hydrogen stations, and hydrogen plants.

What is claimed is:

1. A gas-detecting apparatus comprising:
    a gas sensor that includes:
        a first electrode,
        a second electrode,
        a metal oxide layer disposed between the first electrode and the second electrode, the metal oxide layer including a bulk area and a local area surrounded by the bulk area, a degree of oxygen deficiency of the local area being higher than that of the bulk area, and
        an insulation film covering the first electrode, the second electrode, and the metal oxide layer, the insulation film having an opening from which a surface of the second electrode is exposed; and
    a power supply circuit configured to apply a predetermined voltage between the first electrode and the second electrode, wherein:
        an upper surface of the local area and an upper surface of the bulk area are in direct contact with a bottom surface of the second electrode, and
        a bottom of the local area is away from an upper surface of the first electrode.

2. The gas-detecting apparatus according to claim 1, wherein
    the power supply circuit is configured to apply, before the contact of the gas, the predetermined voltage between the first electrode and the second electrode to cause the metal oxide layer to a high resistive state.

3. The gas-detecting apparatus according to claim 2, wherein
    the power supply circuit further is configured to apply, after the contact of the gas, the predetermined voltage between the first electrode and the second electrode to reset the metal oxide layer to the high resistive state.

4. The gas-detecting apparatus according to claim 1, wherein
    the power supply circuit comprises:
        a first power supply circuit configured to generate the predetermined voltage; and
        a second power supply circuit configured to generate a detection voltage for measuring a resistance value of the metal oxide layer.

5. The gas-detecting apparatus according to claim 4, further comprising a current meter coupled in series with the power supply circuit and the metal oxide layer, and configured to measure a current value flowing between the first electrode and the second electrode.

6. The gas-detecting apparatus according to claim 4, wherein
    the power supply circuit further comprises a switch configured to switch a connection of the gas sensor to the first power supply circuit or the second power supply circuit.

7. The gas-detecting apparatus according to claim 1, wherein
    the exposed surface of the second electrode is exposed to air.

8. The gas-detecting apparatus according to claim 1, wherein
    the metal oxide layer includes a first metal oxide layer being in contact with the first electrode and a second metal oxide layer being in contact with the second electrode, a degree of oxygen deficiency of the first metal oxide layer being higher than that of the bulk area, the second metal oxide layer including the bulk area, and
    the local area is in contact with the second electrode and passes through the second metal oxide layer.

9. The gas-detecting apparatus according to claim 1, wherein
    the second electrode contains at least one selected from the group consisting of platinum, palladium, and iridium.

10. The gas-detecting apparatus according to claim 1, wherein
    the metal oxide layer contains at least one of a transition metal oxide and an aluminum oxide.

11. The gas-detecting apparatus according to claim 10, wherein
    the transition metal oxide is tantalum oxide, hafnium oxide, or zirconium oxide.

12. The gas-detecting apparatus according to claim 1, wherein the local area is formed by applying an initial break voltage between the first electrode and the second electrode.

13. The gas-detecting apparatus according to claim 1, wherein the bulk area of the metal oxide layer is represented by MOx and the local area of the metal oxide layer is represented by MOy, where M is a metal element selected from the group consisting of at least one of a transition metal and aluminum, and x>y.

14. The gas-detecting apparatus according to claim 1, wherein a bottom surface of the bulk area is in direct contact with an upper surface of the first electrode.

15. A method of detecting gas with a gas sensor,
the gas sensor comprising:
   a first electrode;
   a second electrode;
   a metal oxide layer disposed between the first electrode and the second electrode, the metal oxide layer including a bulk area and a local area surrounded by the bulk area, a degree of oxygen deficiency of the local region being higher than that of the bulk area; and
   an insulation film covering the first electrode, the second electrode, and the metal oxide layer, the insulation film having an opening from which a surface of the second electrode is exposed, wherein an upper surface of the local area and an upper surface of the bulk area are in direct contact with a bottom surface of the second electrode, and a bottom of the local area is away from an upper surface of the first electrode,
the method of detecting gas comprising:
   detecting gas containing hydrogen atoms by detecting a reduction in a resistance value of the metal oxide layer; and
   applying a predetermined voltage between the first electrode and the second electrode to increase the resistance value of the metal oxide layer before and/or after the detection of the gas.

16. A gas-detecting apparatus comprising:
a gas sensor that includes:
   a first electrode;
   a second electrode;
   a metal oxide layer disposed between the first electrode and the second electrode; and
   an insulation film covering the first electrode, the second electrode, and the metal oxide layer, the insulation film having an opening from which a surface of the second electrode is exposed; and
a power supply circuit configured to apply a predetermined voltage between the first electrode and the second electrode, wherein:
the metal oxide layer includes
   a first metal oxide layer, a bottom surface of the first metal oxide layer being in direct contact with an upper surface of the first electrode,
   a second metal oxide layer, an upper surface layer of the second metal oxide layer being in direct contact with a bottom surface of the second electrode, and
   a local area passing through the second metal oxide layer, an upper surface of the local area being in direct contact with the bottom surface of the second electrode, a bottom of the local area being away from the upper surface of the first electrode,
a degree of oxygen deficiency of the first metal oxide layer is higher than that of the second metal oxide layer, and
a degree of oxygen deficiency of the local area is higher than that of the second metal oxide layer.

17. The gas-detecting apparatus according to claim 16, wherein the local area is formed by applying an initial break voltage between the first electrode and the second electrode.

18. The gas-detecting apparatus according to claim 16, wherein the first metal oxide layer is represented by MOz, the second metal oxide layer is represented by MOx, and the local area is represented by MOy, where M is a metal element selected from the group consisting of at least one of a transition metal and aluminum, and x>y and x>z.

19. A method of detecting gas with the gas-detecting apparatus according to claim 16, the method comprising:
   detecting gas containing hydrogen atoms by detecting a reduction in a resistance value of the metal oxide layer; and
   causing the power supply circuit to apply the predetermined voltage between the first electrode and the second electrode to increase the resistance value of the metal oxide layer before and/or after the detection of the gas.

* * * * *